United States Patent [19]
Fiolitakis et al.

[11] Patent Number: 5,744,675
[45] Date of Patent: Apr. 28, 1998

[54] PROCESS FOR PREPARING AN OLIGOMER MIXTURE FROM $\alpha,\omega$-DIOLEFINES AND MIXTURE PREPARD.

[75] Inventors: Emmanuel Fiolitakis, Duelmen; Hans Guenther Wey, Muelheim/Ruhr; Jaroslaw Monkiewicz, Rheinfelden, all of Germany

[73] Assignee: Huels Aktiengesellschaft, Marl, Germany

[21] Appl. No.: 571,673

[22] Filed: Dec. 13, 1995

[30] Foreign Application Priority Data

Mar. 8, 1995 [DE] Germany ............... 195 08 088.2

[51] Int. Cl.$^6$ .................... C10M 107/10; C07C 2/30
[52] U.S. Cl. .................. 585/506; 585/507; 585/508
[58] Field of Search ............... 585/506, 507, 585/508

[56] References Cited

U.S. PATENT DOCUMENTS

| | | | |
|---|---|---|---|
| 4,954,125 | 9/1990 | Ono et al. ........................... | 585/508 |
| 5,113,033 | 5/1992 | Myers et al. ........................ | 585/506 |
| 5,306,856 | 4/1994 | Streck et al. ....................... | 585/506 |
| 5,516,958 | 5/1996 | Schaerfl, Jr. et al. ............... | 585/511 |

FOREIGN PATENT DOCUMENTS 41 19 332  12/1992  Germany.

*Primary Examiner*—Jacqueline V. Howard
*Attorney, Agent, or Firm*—Oblon, Spivak, McClelland, Maier & Neustadt, P.C.

[57] ABSTRACT

The process of the invention, using a plurality of passes, divides the crude product of each pass into a part which contains tetramers and higher oligomers and represents the desired product of a pass and at least one further part which contains the major part of the monomers, dimers and trimers and which serves at least in part as part of the starting materials in a subsequent reaction pass. At the same time, the catalyst concentration is increased. In all reaction passes, only a moderate starting material conversion is sought.

15 Claims, No Drawings

PROCESS FOR PREPARING AN OLIGOMER MIXTURE FROM α,ω-DIOLEFINES AND MIXTURE PREPARD.

BACKGROUND OF THE INVENTION

1. Field of the Invention

The present invention relates to a process for preparing an oligomer mixture from α,ω-diolefins in the liquid phase and in the presence of an organoaluminium compound as catalyst. Functional liquids, oils, coatings and adhesives containing an oligomer mixture prepared by this process are also described.

2. Discussion of the Background

DE-A 41 19 332, incorporated herein by reference, discloses a process for preparing α,ω-unsaturated oligomers from α,ω-diolefins. The α,ω-diolefins are reacted in the liquid phase at a temperature between 150° C. and 350° C. with the addition of catalytically active amounts of organoaluminium compounds of the general formula $AlX_3$ or $AlX_2H$. This addition results in the formation of α,ω-unsaturated oligomers containing methylidene groups, from which oligomers biodegradable base oils for lubricants and functional liquids can be obtained, as described in DE-A 43 00 418, also incorporated herein by reference. In addition, valuable raw materials for the surface coatings and adhesives sector can be produced from the oligomers.

The process of DE-A 41 19 332 gives a broad product distribution in the preparation of the oligomers, with over 70% of the oligomers having a degree of oligomerization in the range from 3 to 20. No indication is given of the type of distribution. The product yield of all oligomers fluctuates significantly and is between about 40% and 85%, based on the molar amount of diolefin used.

However, for use in the lubricating oil sector, tetramers, pentamers and hexamers of α,ω-diolefins are of primary interest owing to the special requirements in respect to evaporation losses (low content of low boilers) and viscosity (no excessively high degree of oligomerization).

OBJECTS OF THE INVENTION

It is therefore an object of the present invention to provide a process for preparing an oligomer mixture from α,ω-diolefins which has a narrow product distribution around a degree of oligomerization of from 4 to 5 and thus leads to improved product properties. Other objects will be apparent upon further appreciation of the invention.

DETAILED DESCRIPTION OF THE INVENTION

According to the invention, the above object is achieved by a process for preparing an oligomer mixture in the liquid phase from α,ω-diolefins in the presence of an organoaluminium compound as catalyst. The invention process can, at least conceptually, be divided into at least two temporally successive reaction segments or passes. The reaction product of each of these passes is separated by any conventional separation process (preferably by distillation) into a first part which contains at least the major portion (preferably more than 95% by weight of the total content) of the monomeric α,ω-diolefins present in the crude product, their dimers and also the major part (preferably more than 60% by weight of the total content) of their trimers, and at least a second part which contains at least the tetramers and higher oligomers, as far as possible completely. In general, this separation is preceded by hydrolytic decomposition of the catalyst. As separation process, particular preference is given to molecular distillation to suppress the thermal stressing of the crude product.

A part of the monomers and dimers present in the first, low-boiler-containing part thus obtained is preferably separated therefrom and removed from the process, preferably a proportion of from 20 to 40% by weight of the low-boiler-containing first part. The remainder, together with fresh monomer and, if desired, other additional olefins, serves as starting material for the subsequent reaction pass. Sufficient fresh monomer is added to keep the total number of terminal double bonds in the starting material mixture constant or near constant (i.e., ±10%). To compensate for the reduced reactivity of the reaction mixture caused by the recycle material (i.e. the part of low boilers returned), the concentration of the catalyst used is generally increased from pass to pass, and is increased by up to 20% by weight in each case, based on the mass of catalyst in the preceding pass, preferably by about 12% by weight. In the first pass, the catalyst concentration is generally between 2 and 4 mol %, based on the molar amount of α,ω-diolefins used.

To achieve the desired product composition having a narrow product distribution around a degree of oligomerization of from 4 to 5, it is necessary according to the invention for the following reaction characteristic:

$$\text{catalyst concentration-reaction time,}$$

at least in the first pass, i.e. starting with fresh monomer without recycle material, to assume a value of between 0.10 and 0.16 $(kmol/m^3) \cdot h$, preferably from 0.11 to 0.15 $(kmol/m^3) \cdot h$. The resulting moderate monomer or starting material conversion of preferably from about 50% to 60% of the amount used in the first and all successive reaction passes reduces the formation of heptamers and higher oligomers which broaden the product distribution to an undesired extent. Even the part containing tetramers and higher oligomers separated off after the first reaction pass corresponds, in this preferred embodiment of the process, directly to the product requirements for use in the lubricating oil sector. The number of reaction passes is preferably up to seven. In general, carrying out further reaction passes no longer serves any useful purpose owing to the high catalyst concentration required.

According to the present invention, the reaction can be carried out either neat or in inert solvents. Suitable solvents and suitable catalysts are the materials specified in DE-A 41 19 332. The reaction temperature is preferably between 150° C. and 350° C., more preferably between 180° C. and 210° C.; the reaction pressure is preferably given by the vapor pressure of the reactants which is established at the reaction temperature Monomeric α,ω-diolefins preferably used are 1,4-pentadiene, 1,7-octadiene, 1,9-decadiene, 1,11-dodecadiene or 1,4,9-decatriene, either in pure form or as mixtures.

In addition to the recycle material and the fresh monomer, further monoolefins or diolefins or both can be metered in before one or more passes. The addition of higher (or lower) molecular weight monomers can, by co-oligomerization, vary the product distribution in respect of the molecular weight within wide limits, so that the product can be matched to different requirements. The same effect can be achieved by the metered addition to the above mentioned dienes (1,4-pentadiene, 1,7-octadiene etc.) of α-monoolefins, like 1-butene, 1-pentene, 1-hexene, 1-heptene and 1-octene.

The process of the invention can be operated either batchwise or continuously. In a preferred embodiment of continuous operation, the various reaction passes or segments follow one another directly in a single reactor, with after about three passes a quasi-steady state being established in respect of the starting materials and the product output of each pass, but not in respect of the amount of catalyst required. The transitions between the individual reaction passes can here become so blurred that these can only be separated conceptually, but the process is still referred to as having passes for ease in description.

The process of the invention offers the following advantages:

- A narrow product distribution about a degree of oligomerization of from 4 to 5 is always achieved independently of the monomeric $\alpha,\omega$-diolefin used. The product thus has improved properties for use as base oil for lubricants and functional liquids.
- The product distribution and thus the product properties can be influenced in a targeted manner by metered addition of $\alpha$-monoolefins or other $\alpha,\omega$-diolefins.
- The yield of tetramers, pentamers and hexamers, which represent the actual desired product, is significantly improved and thus the economics of the preparing process are improved.
- The content of heptamers and higher oligomers in the product is reduced.
- Owing to the narrow product distribution, a distillative work-up of the product can be omitted. The total of the parts separated off, which contain the tetramers and higher oligomers, can directly form the desired product.

The process of the invention is further illustrated below by reference to the following examples. These examples are non-limiting, however, and serve only to further explain the invention.

COMPARATIVE EXAMPLE 1

As described in DE-A. 41 19 332, 1,533 g of 1,7-octadiene dissolved in 778 g of cyclohexane are converted in a reactor at 200° C. using diisobutylaluminium hydride (DIBAH) as catalyst. After a reaction time of 2 hours, the reaction mixture has the composition given in Table 1.

The content of tetramers, pentamers and hexamers is about 30% by weight.

EXAMPLE 1

The process of the invention is carried out in one reactor under batch operation conditions for the conversion of 1,7-octadiene. The reaction conditions and the starting material and product compositions of each pass are shown in Tables 2 and 3. The catalyst used is diisobutylaluminium hydride (DIBAH). The reaction is carried out in cyclohexane as solvent. After seven passes, the process is stopped. Adding together all passes gives the product composition shown in Table 1.

The higher yield of tetramers, pentamers and hexamers and the narrower product distribution about a degree of oligomerization of from 4 to 5 in comparison with Comparative Example 1 can clearly be seen.

EXAMPLE 2

The process of the invention is carried out continuously, but not under steady-state conditions, in a single tubular reactor for the conversion of 1,9-decadiene (dissolved in cyclohexane). The reaction volume is 3.2 m³ and the mean residence time per pass in the tubular reactor is about 2 hours.

At the start, 0.08 kmol/min of 1,9-decadiene dissolved in 9.5 kg/min of cyclohexane are first fed as starting material to the flow tube, since at this point in time no recycle material is yet available. As catalyst, 0.0016 kmol/min of DIBAH are added at the start. As soon as the first recycle material is obtained (approximately after the residence time of 2 hours), the supply of fresh monomer as starting material in the feed is reduced to the extent required such that always about the same amount of terminal double bonds are used. At the same time, the amount of catalyst fed in is increased in stages about every 2 hours to the final value of 0.0025 kmol/min in the last (conceptual) pass. From about the third pass, i.e. after about 6 hours, the process operates in a quasi-steady-state mode in respect of the recycle material, the starting materials and the product; only the amount of catalyst varies from pass to pass. As recycle material, about 70% by weight of the total output of low boilers (monomers to trimers of 1,9-decadiene) is then recirculated and again used as part of the starting materials. The reaction characteristic of each pass is about 0.13 (kmol/m³)·h.

The composition of the (desired) product (after separating off the low boilers) in this quasi-steady state is given in Table 1. The proportion of tetramers, pentamers and hexamers in the desired product is about 68% by weight and is thus more than twice as high as in Comparative Example 1. After about 14 hours, the process is interrupted (this corresponds to about 7 passes) and restarted with fresh monomer.

EXAMPLE 3

Using a method similar to Example 2, the process of the invention is used for the continuous, non-steady-state reaction of 1,7-octadiene (dissolved in cyclohexane). The reactor used is, in place of the flow tube, a cascade of vessels consisting of 4 vessels each having a reaction volume of 0.75 m³. The work-up of the crude product with the removal of the low boilers is carried out only at the outlet of the cascade of vessels, not after each vessel. The residence time is about 0.5 h per vessel. For the amount of starting material, the solvent requirement, the catalyst requirement, the degree of recirculation of the recycle material and the reaction characteristic, the figures given in Example 2 again apply.

Here too, for the product output, inter alia, a quasi-steady state is established after about 6 hours. The composition of the desired product (after removal of the low boilers) of a pass is again shown in Table 1. Here too, the proportion of tetramers, pentamers or hexamers is, at about 64% by weight, more than twice as high as in Comparative Example 1. Here too, the process is interrupted after about 14 hours and restarted with fresh monomer.

Both in Example 2 and in Example 3, the significantly narrower product distribution about a degree of oligomerization of from 4 to 5 in comparison with Comparative Example 1 can be seen. In Example 2 and in Example 3, only the composition of the desired product of a quasi-steady-state pass after removal of the low boilers was considered. Naturally, such a work-up is also possible for the product from Comparative Example 1. However, after removing the low boilers, the product would still contain the high proportion LO of heptamers and higher oligomers which, in comparison with the process of the invention, significantly broadens the product distribution and reduces the yield of tetramers, pentamers and hexamers.

This application is based on German Application 195 08 088.2 filed Mar. 8, 1995, incorporated herein by reference.

TABLE 1

Product compositions

| Oligomers | Prior art Comparative Example 1 % by wt. | Process according to the invention |  |  |
|---|---|---|---|---|
| | | Example 1 % by wt. | Example 2 % by wt. | Example 3 % by wt. |
| Monomers | 9.5 | 8.9 | negligible | negligible |
| Dimers | 6.9 | 8.8 | negligible | negligible |
| Trimers | 7.2 | 14.1 | 12.7 | 13.0 |
| Tetramers | 10.6 | 19.8 | 33.4 | 31.3 |
| Pentamers | 10.6 | 16.3 | 20.9 | 19.6 |
| Hexamers | 8.9 | 11.7 | 13.7 | 13.4 |
| Heptamers | 8.9 | 20.4 | 7.7 | 7.9 |
| Octamers | 6.5 | | 5.2 | 5.8 |
| Nonamers and higher | 30.9 | | remainder | remainder |

TABLE 2

Example 1 - Starting materials of the passes

| | Starting materials | | | | | | | | | |
|---|---|---|---|---|---|---|---|---|---|---|
| | Fresh | From the previous pass | | | | | Total | | Solvent | | |
| Test No. | 1,7-octadiene [g] | Monomers [g] | Dimers [g] | Trimers [g] | Others [g] | Mass [g] | molar amount [mol] | Cat. DIBAH [mol] | cyclo-hexane [g] | Temp. [°C.] | React. time [min] |
| 1 | 880 | — | — | — | — | 880 | 8 | 0.16 | 952 | 200 | 120 |
| 2 | 511 | 252 | 172 | 92 | 2 | 1029 | 8 | 0.17 | 952 | 200 | 120 |
| 3 | 576 | 187 | 159 | 122 | 6 | 1050 | 8 | 0.19 | 952 | 200 | 120 |
| 4 | 467 | 265 | 226 | 115 | 10 | 1083 | 8 | 0.22 | 952 | 200 | 120 |
| 5 | 434 | 277 | 218 | 185 | 15 | 1129 | 8 | 0.25 | 952 | 200 | 120 |
| 6 | 446 | 255 | 226 | 202 | 11 | 1140 | 8 | 0.28 | 952 | 200 | 120 |
| 7 | 195 | 142 | 131 | 119 | 9 | 596 | 4 | 0.14 | 476 | 200 | 120 |

TABLE 3

Example 1 - Products of the passes

| Test No. | Monomers [g] | Dimers [g] | Trimers [g] | n = 4 [g] | n = 5 [g] | n = 6 [g] | n ≥ 7 [g] | Others [g] | Total mass [g] | % of the mass used |
|---|---|---|---|---|---|---|---|---|---|---|
| 1 | 280 | 192 | 163 | 63 | 54 | 31 | 36 | 3 | 821 | 93 |
| 2 | 187 | 163 | 166 | 105 | 98 | 72 | 157 | 6 | 948 | 92 |
| 3 | 265 | 232 | 159 | 91 | 64 | 42 | 49 | 10 | 912 | 87 |
| 4 | 277 | 221 | 195 | 89 | 80 | 59 | 84 | 15 | 1020 | 94 |
| 5 | 258 | 248 | 230 | 92 | 74 | 46 | 58 | 11 | 1017 | 90 |
| 6 | 180 | 168 | 181 | 101 | 84 | 80 | 197 | 11 | 1002 | 88 |
| 7 | 190 | 164 | 152 | 35 | 20 | 10 | 14 | 14 | 599 | 100 | n = degree of oligomerization

What is claimed as new and is desired to be secured by Letters Patent of the United States is:

1. A process for preparing an oligomer mixture from α,ω-diolefins in the presence of an organoaluminum compound as a catalyst in the liquid phase, said process comprising:

a) reacting said α,ω-diolefins with at least two successive reaction passes;

b) separating reaction product of each pass into a first part which contains at least, based on the total content and the reaction product, more than 95% by weight of the monomeric α,ω-diolefins and their dimers and more than 60% by weight of their trimers, and into at least a second part which contains at least the tetramers and higher oligomer, at least a part of the separated monomeric α,ω-diolefins, dimers and trimers from the first part being a part of the starting materials for a subsequent pass such that the total of the terminal double bonds remains constant or almost constant in each pass; and c) increasing the catalyst concentration from pass to pass by up to 20% by weight based on the weight of the catalyst in the preceding pass; and wherein said reaction has a reaction characteristic value defined as (catalyst concentration reaction time) between about 0.10 kmol/m$^3$·h and 0.16 kmol/m$^3$·h for at least the first pass.

2. The process according to claim 1, wherein the reaction characteristic value is between 0.11 (kmol/m$^3$)·h and 0.15 (kmol/m$^3$)·h in the first pass.

3. The process according to claim 1, wherein organoaluminium compounds of the formula AlX$_3$ or AlX$_2$H are said catalyst, where X is an aliphatic, alicyclic or aromatic hydrocarbon substituent having from 1 to 30 carbon atoms.

4. The process according to claim 1, wherein the catalyst concentration in the first pass is between 2 and 4 mol % based on the molar amount of α,ω-diolefins.

5. The process according to claim 1, wherein the reaction temperature is between 180° C. and 210° C. and the pressure corresponds to the vapor pressure of the reactants established at this temperature.

6. The process according to claim 1, wherein crude product from each pass is first subjected to a hydrolytic decomposition of the catalyst.

7. The process according to claim 1, wherein the separation into parts is carried out by distillation.

8. The process according to claim 1, wherein
   (a) after each pass the monomers and dimers are separated off completely or almost completely and the trimers are separated off to an extent of more than 60% of the total content in the crude product and
   (b) after separation in (a) from 60 to 80% of each of these separated monomers and dimers and all or almost all separated trimers are used as part of the starting materials.

9. The process according to claim 1, wherein the reaction is carried out neat or in an inert solvent.

10. The process according to claim 1, wherein the process is carried out continuously or batchwise.

11. The process according to claim 1, wherein 1,4-pentadiene, 1,7-octadiene, 1,9-decadiene, 1,11-dodecadiene or 1,4,9-decatriene are used as monomeric $\alpha,\omega$-diolefins.

12. The process according to claim 1, wherein the molecular mass of the product oligomer mixture is controlled by addition of $\alpha$-monoolefins or by co-oligomerization with $\alpha,\omega$-diolefins having the same or a different hydrocarbon chain length compared to the main monomer.

13. A biodegradable base oil, functional liquid, coating or adhesive comprising an oligomer mixture prepared according to the process of claim 1.

14. An oligomer mixture prepared according to the process of claim 1.

15. The process according to claim 1, wherein in step c), the catalyst concentration is increased from pass to pass by about 12% by weight.

* * * * *

UNITED STATES PATENT AND TRADEMARK OFFICE
CERTIFICATE OF CORRECTION

PATENT NO. : 5,744,675
DATED : April 28, 1998
INVENTOR(S) : Emmanuel FIOLITAKIS, et al.

It is certified that error appears in the above-identified patent and that said Letters Patent is hereby corrected as shown below:

On the title page item [54] & on the top of Column 1, the last word of the Title should be:

--PREPARED--

Signed and Sealed this

Twenty-second Day of September, 1998

Attest:

BRUCE LEHMAN

Attesting Officer       Commissioner of Patents and Trademarks